US012636017B2

(12) United States Patent　　(10) Patent No.: US 12,636,017 B2
Tepic et al.　　(45) Date of Patent: May 26, 2026

(54) SURGICAL OSCILLATING SAW BLADES

(71) Applicant: Kyon AG, Zürich (CH)

(72) Inventors: Slobodan Tepic, Klosters Dorf (CH); Reto Hitz, Aristau (CH); Stephen Bresina, Davos Dorf (CH)

(73) Assignee: Kyon AG (CH)

( * ) Notice: Subject to any disclaimer, the term of this patent is extended or adjusted under 35 U.S.C. 154(b) by 28 days.

(21) Appl. No.: 18/292,694

(22) PCT Filed: Jul. 28, 2022

(86) PCT No.: PCT/EP2022/071197
　　§ 371 (c)(1),
　　(2) Date: Jan. 26, 2024

(87) PCT Pub. No.: WO2023/006878
　　PCT Pub. Date: Feb. 2, 2023

(65) Prior Publication Data
　　US 2025/0082341 A1　　Mar. 13, 2025

(30) Foreign Application Priority Data
　　Jul. 29, 2021　　(EP) ..................................... 21188554

(51) Int. Cl.
　　*A61B 17/14*　　(2006.01)
(52) U.S. Cl.
　　CPC ................................... *A61B 17/142* (2016.11)
(58) Field of Classification Search
　　CPC ... A61B 17/14; A61B 17/142; A61B 17/1637; B23D 61/006
　　See application file for complete search history.

(56) References Cited

U.S. PATENT DOCUMENTS

| | | | | |
|---|---|---|---|---|
| 3,872,561 | A * | 3/1975 | Pomernacki | ......... B23D 61/121 |
| | | | | 407/18 |
| 4,677,973 | A | 7/1987 | Slocum | |
| 4,955,888 | A | 9/1990 | Slocum | |
| 9,527,146 | B2 * | 12/2016 | Stoddart | .............. B23D 61/021 |
| 10,702,283 | B2 | 7/2020 | Sidebotham et al. | |
| 11,919,100 | B2 * | 3/2024 | Novak | ................. B23D 61/006 |
| 2004/0243136 | A1 * | 12/2004 | Gupta | .................. B23D 61/121 |
| | | | | 606/82 |
| 2006/0272468 | A1 * | 12/2006 | Gupta | ................... B27B 19/006 |
| | | | | 83/835 |
| 2011/0288555 | A1 * | 11/2011 | Szanto | .............. A61B 17/1637 |
| | | | | 606/84 |

(Continued)

FOREIGN PATENT DOCUMENTS

| | | | | |
|---|---|---|---|---|
| CN | 117835922 | A * | 4/2024 | ........... A61B 17/142 |
| DE | 102009046907 | A1 * | 5/2011 | ......... B23B 51/0406 |

(Continued)

OTHER PUBLICATIONS

R. Boudrieau, "Tibial Plateau Leveling Osteotomy or Tibial Tuberosity Advancement?", Invited Review, Veterinary Surgery, 38: 2009, 1-22 (22 pages).

(Continued)

*Primary Examiner* — Eric S Gibson
(74) *Attorney, Agent, or Firm* — Klarquist Sparkman, LLP

(57) ABSTRACT

The present invention provides an improved surgical instrument for performing bone osteotomies with reduced heat generation.

15 Claims, 7 Drawing Sheets

(56)                 References Cited

U.S. PATENT DOCUMENTS

| | | | | |
|---|---|---|---|---|
| 2012/0230788 A1* | 9/2012 | Bozic | .................. | B23D 61/121 |
| | | | | 83/849 |
| 2015/0096422 A1* | 4/2015 | Stoddart | .............. | B23D 61/021 |
| | | | | 83/835 |
| 2016/0100846 A1* | 4/2016 | Motherway | .......... | A61F 2/4609 |
| | | | | 606/81 |
| 2018/0125503 A1* | 5/2018 | Sidebotham | ......... | A61B 17/147 |
| 2020/0405495 A1* | 12/2020 | Gatrell | .................. | A61B 17/17 |
| 2021/0276111 A1* | 9/2021 | Novak | ................. | A61B 17/144 |
| 2022/0160371 A1* | 5/2022 | Huwais | .............. | A61B 17/1644 |
| 2025/0082341 A1* | 3/2025 | Tepic | .................. | A61B 17/142 |

FOREIGN PATENT DOCUMENTS

| | | | | | |
|---|---|---|---|---|---|
| EP | 2 214 571 | B1 | 8/2010 | | |
| EP | 2 854 677 | B1 | 4/2015 | | |
| EP | 4124304 | A1 * | 2/2023 | .......... | A61B 17/142 |
| FR | 2656788 | A1 | 7/1991 | | |
| WO | 9301751 | A1 | 2/1993 | | |
| WO | 2007045993 | A2 | 4/2007 | | |
| WO | 2007045993 | A3 | 4/2007 | | |
| WO | WO-2011060978 | A1 * | 5/2011 | ........ | B23B 51/0406 |
| WO | WO-2015048880 | A1 * | 4/2015 | .......... | B23D 61/006 |
| WO | 2016204401 | A1 | 12/2016 | | |
| WO | 2017106093 | A1 | 6/2017 | | |
| WO | WO-2019046561 | A1 * | 3/2019 | ............. | A61B 17/00 |
| WO | WO-2020210442 | A1 * | 10/2020 | ........ | A61B 17/1615 |
| WO | WO-2023006878 | A1 * | 2/2023 | .......... | A61B 17/142 |

OTHER PUBLICATIONS

B. Slocum, et al., "Tibial Plateau Leveling Osteotomy for Repair of Cranial Cruciate Ligament Rupture in the Canine", Stifle Surgery, vol. 23, No. 4, Jul. 1993, 777-795, 1993 (19 pages).

S. Tepic, et al., Biomechanics of the Stifle Joint, in Proceedings of the 1st World Orthopaedic Veterinary Congress, Munich, Sep. 5-8, 2002, 189-190 (2 pages).

B. Slocum, et al. "Cranial tibial wedge osteotomy: A technique for eliminating cranial tibial thrust in cranial cruciate ligament repair", JAVMA, vol. 184, No. 5, Mar. 1, 1984, (6 pages).

International Search Report and Written Opinion issued in PCT/EP2022/071197 dated Nov. 18, 2022, 13 pgs.

* cited by examiner (a)

12a (b)

12b

A-A

Detail A

A (a)

(b)

SURGICAL OSCILLATING SAW BLADES

This application is a 35 U.S.C. 371 National Phase Entry Application from PCT/EP2022/071197 filed Jul. 28, 2022, which claims priority to and the benefit of European Patent Application No. 21188554.6 filed on Jul. 29, 2021, the disclosures of which are incorporated herein by reference in their entirety.

FIELD OF THE INVENTION

The present invention relates to a surgical saw blade useful in performing osteotomies such as Tibial Plateau Leveling Osteotomy (TPLO) with improved geometry of the saw teeth to reduce heat generated by cutting the bone and increase the speed of cutting. The same design improvements can be applied to other, more commonly used oscillating flat surgical saws.

BACKGROUND OF THE INVENTION

The anterior cruciate ligament (ACL) in the human knee joint, commonly called the cranial cruciate ligament (CrCL) in the canine stifle, is frequently torn in trauma. It also frequently fails, particularly in dogs, after a degenerative process of still unknown etiology.

In human orthopedics, standard procedures replace the failed ACL with an ACL allograft or an autograft made from a part of the patient's own patellar tendon or a part of the fascia and tendon removed from the hamstring muscles. The procedure results in a stable knee short-term, but the long-term performance of the knee is often unsatisfactory. Roughly, 75-90% of cases result in degenerative arthritis of the joint within 15 years of the procedure.

In dogs, the standard procedure involves either placement of an extra-capsular suture or performing of one of several geometry-modifying surgical techniques. In the extra-capsular procedure, a suture is placed outside of the joint, usually on the lateral side, to approximate the function of the CrCL. The intention of the suture application is to provide stability of the joint for several weeks while waiting for fibrosis to occur around the joint. This fibrosis should then provide for long-term stability. However, the extra-capsular suture technique regularly results in failure. Degenerative arthritis of the joint, after a year or so, is the rule rather than the exception.

Attempts to replace the CrCL in the dog by an anatomically placed, intra-articular artificial ligament have also generally failed in spite of years of research and development of materials, anchor designs, and surgical techniques.

In surgical, geometry-modifying techniques, the tibia is cut and a segment of it is repositioned to change the geometry of the tibia and/or the joint in order to stabilize the stifle. Various techniques have been used, including tibial plateau leveling osteotomy (TPLO; see U.S. Pat. No. 4,677, 973 and Slocum and Slocum, *Vet. Clin. North Am.* 23:777-795, 1993), cranial closing wedge osteotomy (CWO; Slocum and Devine, *J. Am. Vet. Med. Assoc.* 184:564-569, 1984), and tibial tuberosity advancement (TTA; Tepic et al., *Biomechanics Of The Stifle Joint*, in Proceedings of the 1st World Orthopaedic Veterinary Congress, Munich, Germany, pp. 189-190. 2002; see EP 2854677 B1, Tepic and Hopmans). Of the surgical approaches used in dogs, TTA seems to be associated with less morbidity and faster recovery, and it also provides immediate and durable stability to the joint (Boudrieau, *Vet Surg.*, 38 (1): Jan. 22, 2009). TPLO with more than a decade advantage in terms of clinical acceptance is the most commonly used geometry-modifying procedure.

Nevertheless, surgical complications are not uncommon with all these techniques. The most common is post-surgical damage to the medial meniscus caused by excessive, supra-physiological movement between the femur and the tibia. Failure of the fixation of TPLO by special plates and screws is relatively rare, but when it does occur, it is almost always on the proximal segment and is very difficult to treat by a revision procedure for lack of good bone purchase proximally to the osteotomy. Healing of the bone across the osteotomy can be compromised by thermal necrosis caused by the surgical blade. Cooling by saline during osteotomy is mandatory but only partially effective. A common sign of thermal necrosis is appearance of a sclerotic bone along the cut. The bone killed by excessive temperature shows increased density as mineral deposits fill in all voids left by dead bone cells and capillaries. Lack of blood supply in this zone impedes healing across the osteotomy and also increases the risk of bone infection. Bacterial contamination of dead bone either during surgery or later, by hematogenous spread, can lead to a clinically relevant infection in absence of an immune response or pharmacological intervention both of which require blood perfusion.

All of this also applies to TTA even though the osteotomy for TTA is performed by a flat oscillating blade and can be carried out with more control over the cut and with more effective cooling by saline.

While most of these orthopedic procedures are elective, the infection rates seem to be higher than in surgically treated fractures. This is certainly not what one would expect-fractures are highly variable, involving larger volumes of damaged tissue and on average result in longer surgery times It was an object of the present invention to overcome disadvantages associated with present orthopedic procedures and thereby reduce damage to tissues and/or bones, reduce complications caused by infections and improve healing.

SUMMARY OF THE INVENTION

An aspect of the present invention relates to an oscillating bone saw blade with a rake angle in the range from –5 to 20 degrees on at least some of the saw blade teeth. In certain embodiments, the rake angle is in the range from 0 to 15 degrees on at least some of the saw blade teeth and particularly in the range from 5 to 10 degrees on at least some of the saw blade teeth. In certain embodiments, the rake angle is in the above ranges on all of the saw blade teeth.

The term "oscillating bone saw blade" in the context of the present invention refers to a saw blade adapted for an oscillatory movement. The saw blade of the present invention is adapted to cut a bone during an orthopedic procedure, e.g. procedure involving cutting the tibia, e.g. a TPLO procedure in veterinary medicine. In particular embodiments, the saw blade is adapted to perform orthopedic procedures on dogs. In further particular embodiments, the saw blade is adapted to a cylindrical cut, particularly to a cylindrical cut in a TPLO procedure.

In certain embodiments, the oscillating bone saw blade has a positive relief angle on at least some of the saw blade teeth, e.g., from 5 to 15 degrees, preferably about 10 degrees. In certain embodiments, the release angle is in the above range on all of the saw blade teeth.

In certain embodiments, the oscillating bone saw blade has all the teeth oriented to cut in the same direction. In further embodiments, the oscillating bone saw blade has the teeth oriented to cut in opposing directions, preferably with about a half of the teeth cutting in each direction. In still further embodiments, the oscillating bone saw blade has the teeth shaped to cut in both directions.

In certain embodiments, the oscillating bone saw blade is a dome saw blade having a spherical shape. In further embodiments, the oscillating bone saw blade is a flat or planar saw blade.

The oscillating bone saw blade is typically made of a metal, e.g., stainless steel. Typically, the saw blade is sterilized and optionally sterile packaged to be suitable for use in a medical procedure.

The length of the oscillating bone saw blade is typically about 2 cm to about 10 cm.

The number of teeth of the oscillating bone saw blade is dependent on the cutting width of the saw blade. The width of the saw blade is typically about 0.5 cm to about 2 cm.

The distance between two teeth of the saw blade is typically about 0.5 mm to about 3 mm, particularly about 0.7 mm to about 2 mm and more particularly about 1 mm to about 1.5 mm.

The depth from the tip of the tooth to the base of the tooth is typically about 0.3 mm to 1.5 mm.

The radius of the saw for a cylindrical cut is typically provided from about 9 mm to about 33 mm in 3 mm steps. The most common radii for the TPLO procedure are 21 mm and 24 mm.

The oscillating bone saw blade of the invention may be mounted on a drive unit. The drive unit may comprise a power source, e.g., a battery, a charger, an electrical power and/or an electrical connection, or compressed air. In certain embodiments, the saw blade is adapted to be operated with a power from about 30 Watts to about 300 Watts.

In certain embodiments, the total amplitude of oscillation of the drive unit is about 4 to 8 degrees, particularly about 6 degrees.

A further aspect of the present invention is an oscillating bone saw comprising an oscillating saw blade as described above and a drive unit. The saw is adapted for performing a surgical procedure, particularly an orthopedic procedure such as a procedure involving cutting the tibia, e.g., a TPLO procedure, in veterinary medicine.

A further aspect of the present invention is a method of performing a bone surgery in human or veterinary medicine, comprising cutting a bone with an oscillating saw blade as described above.

The present invention provides a surgical instrument with improved performance, which should lead to better clinical outcomes in hundreds of thousands of orthopedic procedures performed annually in veterinary and human patients. The number of corrective osteotomies for cruciate disease in dogs by TPLO or TTA is in the order of 200'000 per year. Even though the complication rates are relatively low, the number of cases that suffer from morbidities associated with infections or delayed healing are significant and partially responsible for reluctance of veterinary professionals and dog owners to opt for the geometry modifying procedures instead of less invasive suturing techniques that are less effective in resolving the problems of cruciate deficiency. Suturing techniques account for 80 to 90% of all treatments performed for cruciate ligament ruptures in dogs.

For performing the TPLO osteotomy, Slocum adopted and then modified an oscillating autopsy saw. Slocum and de Soutter Medical Company developed an axially aligned power saw and blade remaining the most commonly used type by TPLO surgeons. Slocum's bi-radial saw blade has been replaced by a variety of constant thickness blades used with either axially aligned oscillating motor units or with power drills with oscillation adapters. In all cases known to the inventors, the basic shape of the cutting teeth has not changed. The rake angle is negative in the range from 20 to 30 degrees for cutting in both directions resulting in pointed tip of the tooth and thus undefined relief angle.

Cutting into bone with a saw of these basic geometric parameters is however highly inefficient resulting in high heat production. In fact, the action is more akin to crushing the bone rather than cutting into it. Bone debris is pushed down into extant bone under the advancing saw tooth. This shape of tooth could not possibly cut into hard materials such as metals. Saw teeth of this shape can remove wood and are commonly used on oscillating blades used for minor cutting jobs in carpentry.

This invention applies the knowledge from industrial applications to surgical oscillating saws, to TPLO saws specifically but also more broadly to flat oscillating saw blades for planar osteotomies. In addition to cutting with reduced power dissipation that is harmful to the bone, unidirectional cutting action provides another, important advantage.

Back and forth reaction force produced by conventional oscillating saw blades needs a large inertia of the power unit to counteract the force of the cutting. Power units can be made with highly efficient electric or pneumatic motors with low mass (inertia) but they lose efficiency because they will oscillate in the direction opposite to the movement of the blade. Hands of the surgeon holding the power unit cannot produce much resistance to the oscillatory movement since the coupling between the hand(s) and the power unit is subject to highly non-linear stiffness of the skin and underlying muscles. For small displacements that oscillating power unit produces—only a few degrees of rotation—the stiffness of the hand tissue is very low providing no benefit of the inertia that hand and arm of the surgeon could otherwise provide. However, if the saw is cutting into bone only when it moves in one direction, the power unit will drive the tissue of the hand into its higher stiffness range and thus provide additional resistance to oscillation of the power unit and with that increase the amplitude of the saw blade closer to its theoretical range.

The same applies to the bone being cut. It is mostly supported by soft tissues and connected to other bones at the joints, all of it of high compliance for small displacements. The inertia of the bone also reduces inversely with a third power of linear dimensions so cutting across small bones with oscillating saws becomes even more of a challenge.

Using saws that cut only in one direction pushes the bone into stiffer support by the surrounding soft tissue as well as the hand piece of the power unit into opposite direction of the operator's hand. This gives engineers extra freedom to design power units with lower moment of inertia and hence weight. It is also possible to design oscillating mechanisms with asymmetric cycle whereby the return, idle stroke runs faster than the cutting stroke. This can partially offset the handicap of cutting in only one direction.

DETAILED DESCRIPTION

Figure 1:
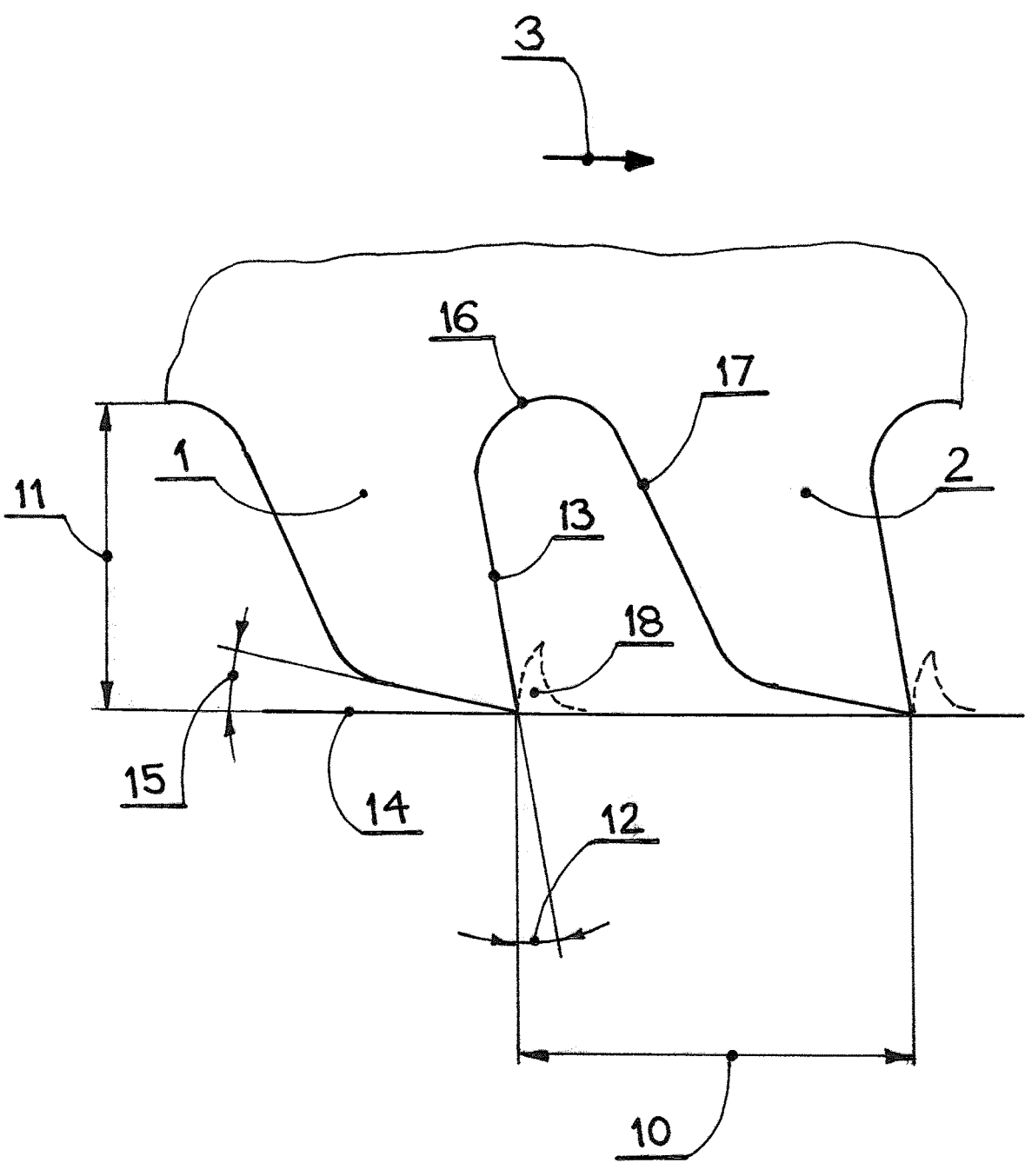
FIG. 1 shows a saw blade tooth geometry with relevant angles.

The basic geometry of a saw tooth is defined by 4 parameters, FIG. 1. The distance 10 from tooth 1 to tooth 2, the depth 11 from the tip of the tooth to the base of the tooth, the rake angle 12 between the cutting front of the tooth 13 and the normal to the surface 14 of the material being cut, and the relief angle 15 between the back of the cutting tooth and the surface 14. The base 16 of the tooth and the backside 17 of the cutting tooth are of lesser impact for the function of the saw but should be shaped to allow as much volume for the cutting chips without causing undue stress concentrations that could cause failure of the saw. Shown on FIG. 1 is a positive rake angle 12, which lifts the chips 18 of the material into the volume between the teeth. Direction of the movement of the saw when cutting is denoted by arrow 3.

Figure 2:
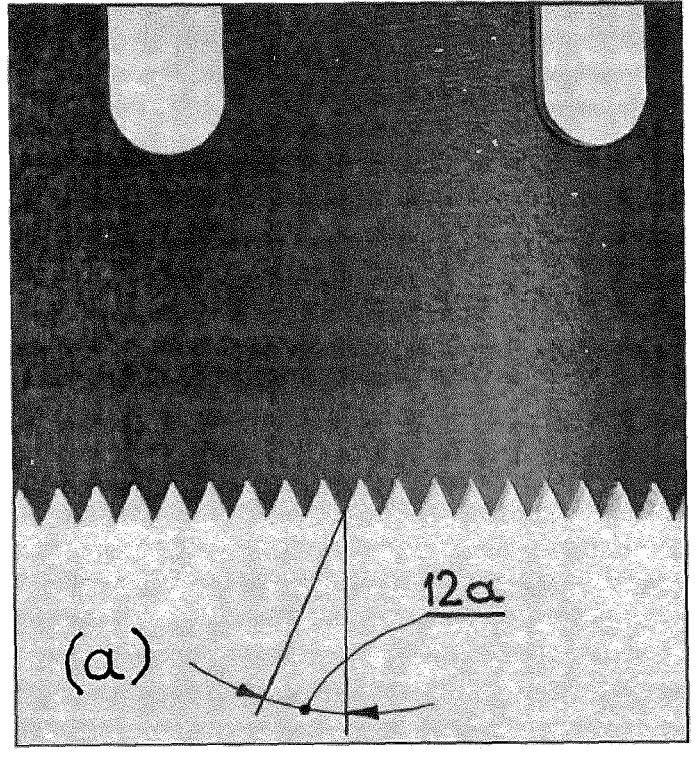
FIG. 2 photographs show the geometry of the state-of-the-art teeth of two TPLO blades from the leading brand suppliers of instruments for veterinary surgery.
Figure 2:
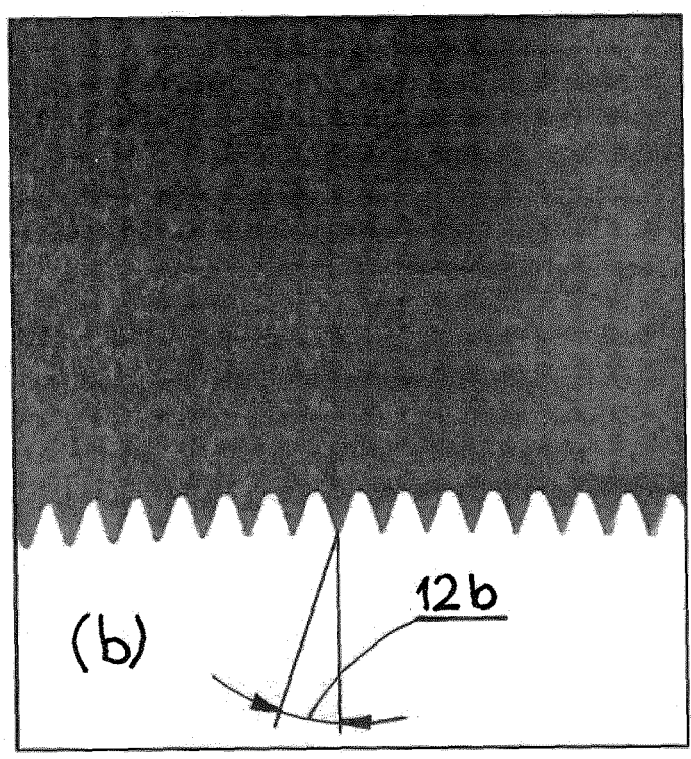

There are many TPLO saws on the veterinary market—two of the leading brands are shown on photographs in FIG. 2. Both have negative rake angles as marked in FIG. 2, and both have pointed tips thus leaving undefined relief angle. The rake angle of the blade (a) on FIG. 2 is about −25 degrees; of the blade (b) on FIG. 2 it is about −20 degrees. To the best knowledge of the present inventors all TPLO saws have these same geometrical features and the patents and patent applications do not reveal anything different (D. Barclay Slocum, U.S. Pat. No. 4,955,888; Zsigmond Szanto, EP 2 214 571 B1, 2016; Chrisopher G. Sidebotham, et al., U.S. Pat. No. 10,702,283 B2, 2020). Szanto discloses an oscillating saw blade for cutting spherical or dome osteotomies that can also be used for a TPLO procedure as well as for some other orthopedic applications.

Figure 3:
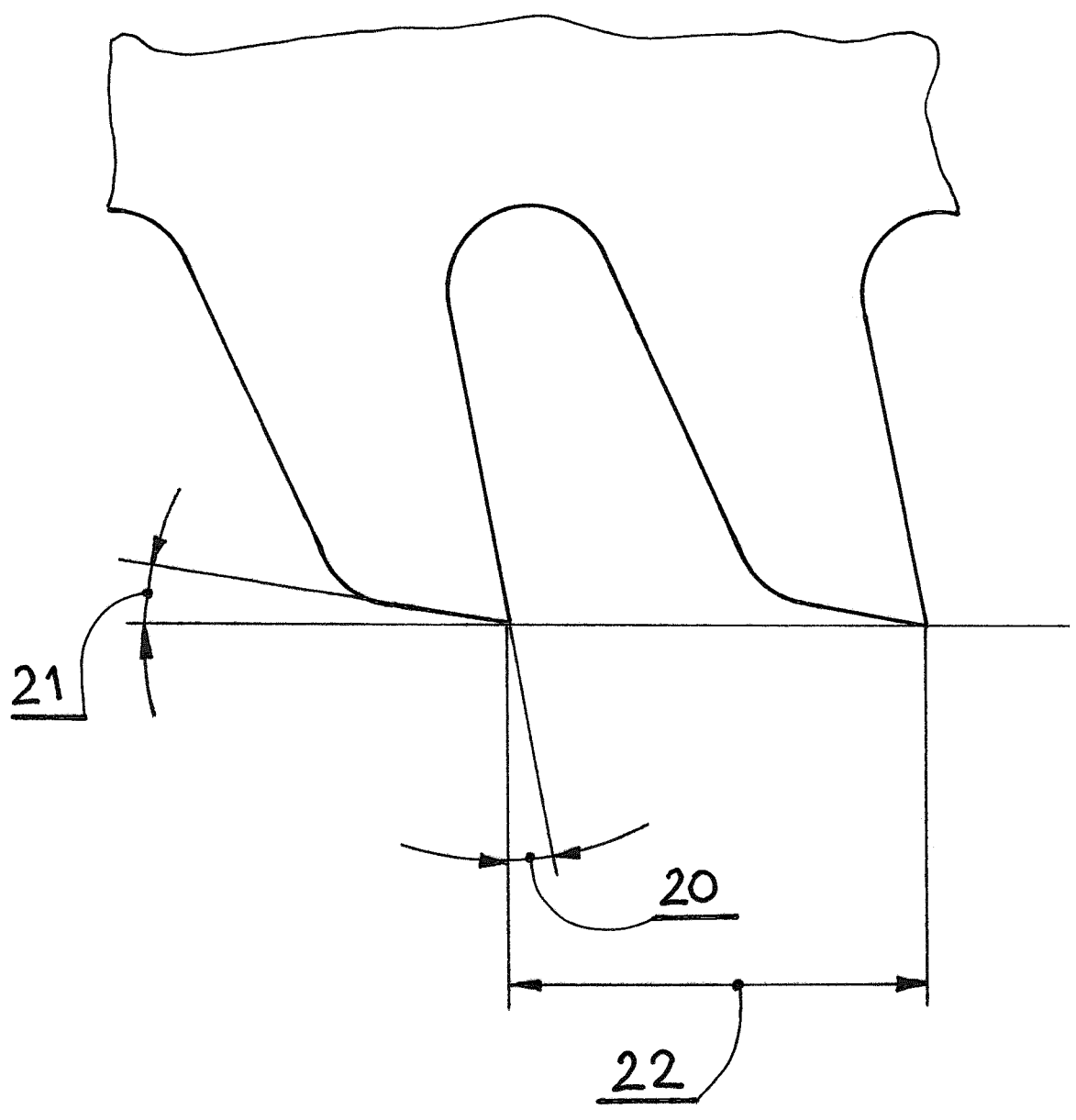
FIG. 3 shows the basic geometry of the TPLO saw blade teeth according to this invention.

The saw teeth for TPLO blades of this invention preferably have a positive rake angle 20, FIG. 3, as well as a positive relief angle 21. A small negative rake angle can be used if less aggressive cutting is aimed for. The range of the rake angle is -5 to 20 degrees, preferably 0 to 15 degrees, and most preferably 5 to 10 degrees. The relief angle is from 5 to 15 degrees, preferably about 10 degrees. The distance or spacing 22 from tooth to tooth depends on the radius of the blade but in all cases, it should be smaller than the amplitude of oscillation of the drive unit. For example, if the total amplitude of oscillation of the drive unit is 6 degrees and the radius of the saw is 24 mm, the spacing of the teeth should be smaller than 24×6.28×6/360=2.5 mm, and preferably about a half of that considering that the theoretical oscillation amplitude is always reduced due to compliant coupling between the drive unit and operator, the bone and the rest of the patient's body, and limited inertias of both the bone and the drive unit.

Figure 4:
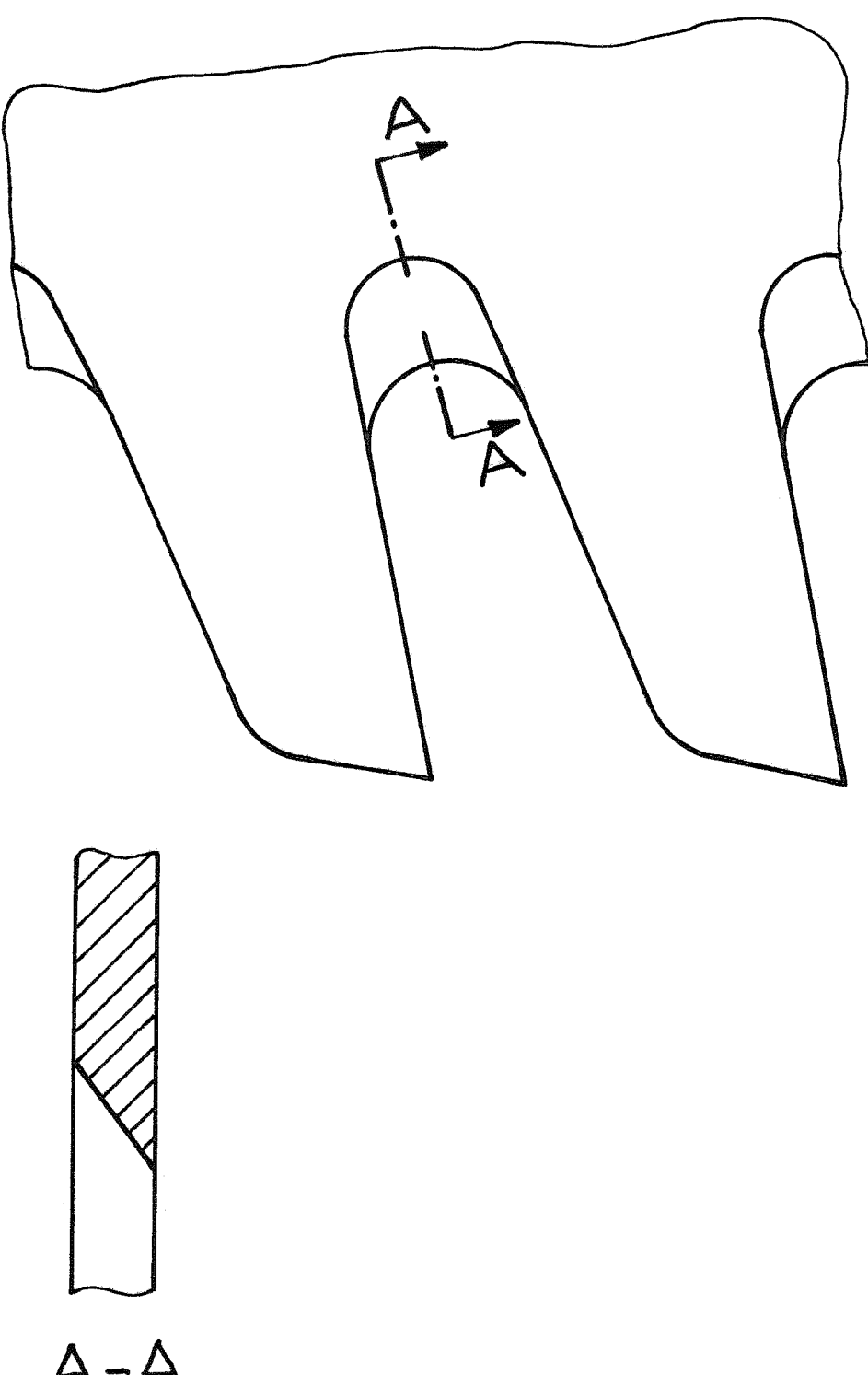
FIG. 4 shows the saw blade teeth according to this invention with improved clearance of bone chips.

Effective use of a saw blade on bones calls for repeated movement of the blade in and out from the saw cut in order to clear the bone chips that otherwise will fill in the volume between the teeth and prevent the blade from advancing deeper into the bone. It is of same advantage to direct the chips sideways, out from the free volume between the teeth. Shown on FIG. 4 is one way of achieving this. The base of the tooth is cut at an angle pushing the chips sideways.

Figure 5:
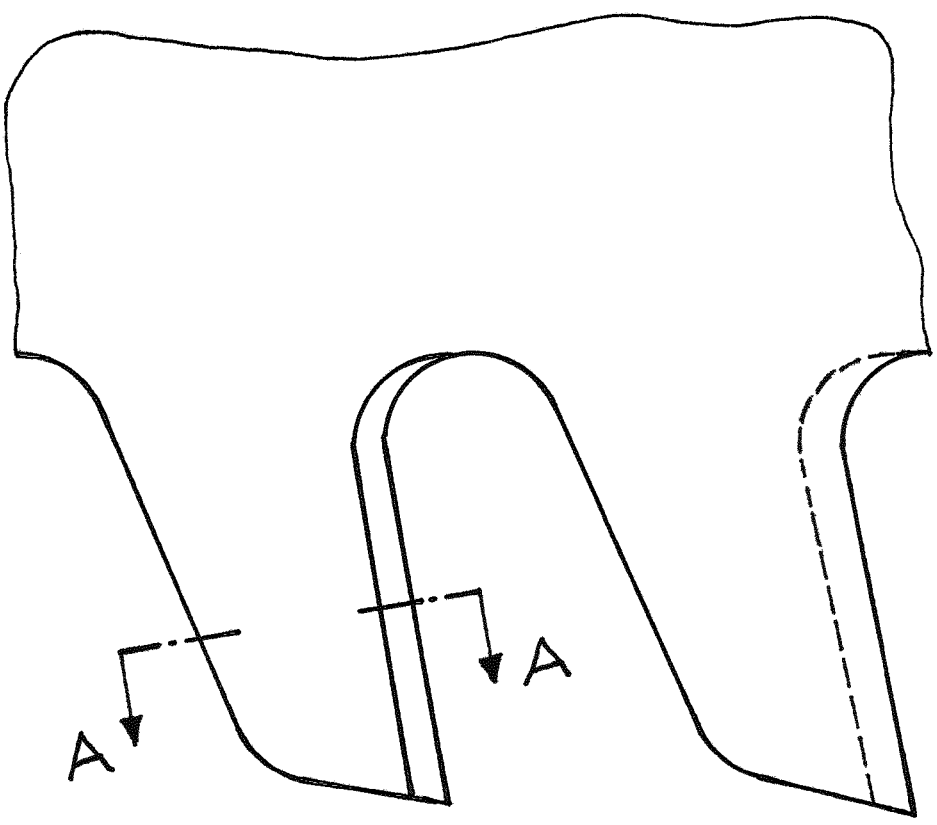
FIG. 5 shows the saw blade teeth according to this invention with another means for improved clearance of bone chips.
Figure 5:
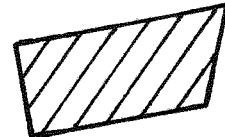

On FIG. 5, the cutting face of the tooth is angled sideways causing the chips to move sideways too. This angle can alternate left and right from tooth to tooth, as shown.

It is also customary to make the width of the cut be wider than the base thickness of the saw either by pushing teeth out from the plane of the saw alternating this from tooth to tooth, or by making the saw blade thinner in the direction away from the teeth. The later method is preferred for surgical saws.

Figure 6:
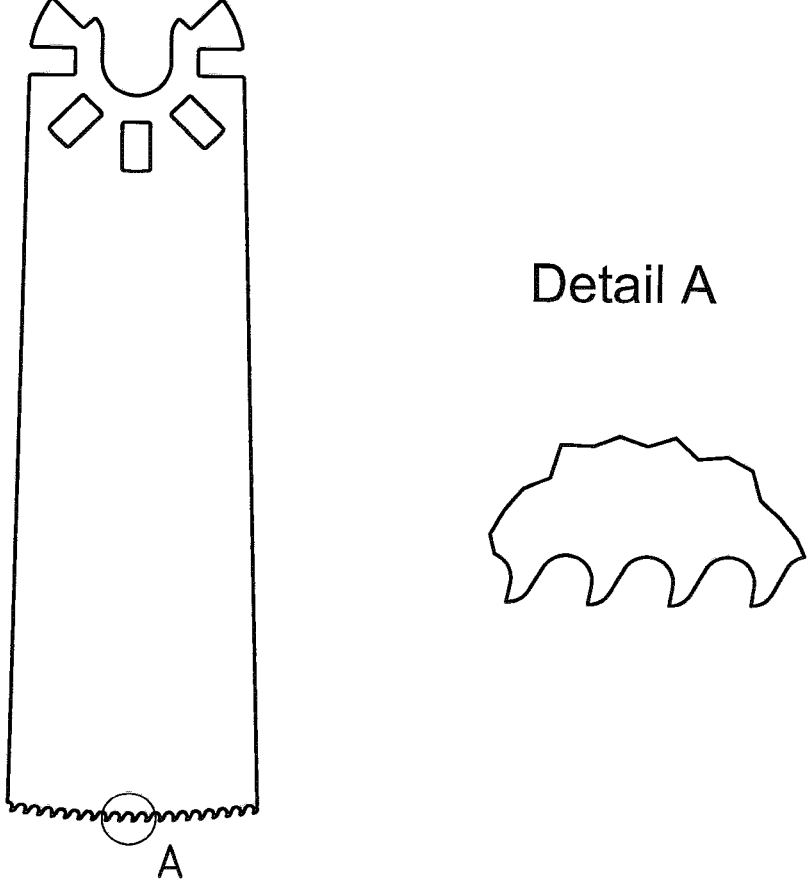
FIG. 6 shows a perspective view of a planar, oscillating saw blade with the saw tooth detail.

All of these learnings applied to the TPLO saw can also be applied to planar oscillating bone saws, FIG. 6.

Figure 7:
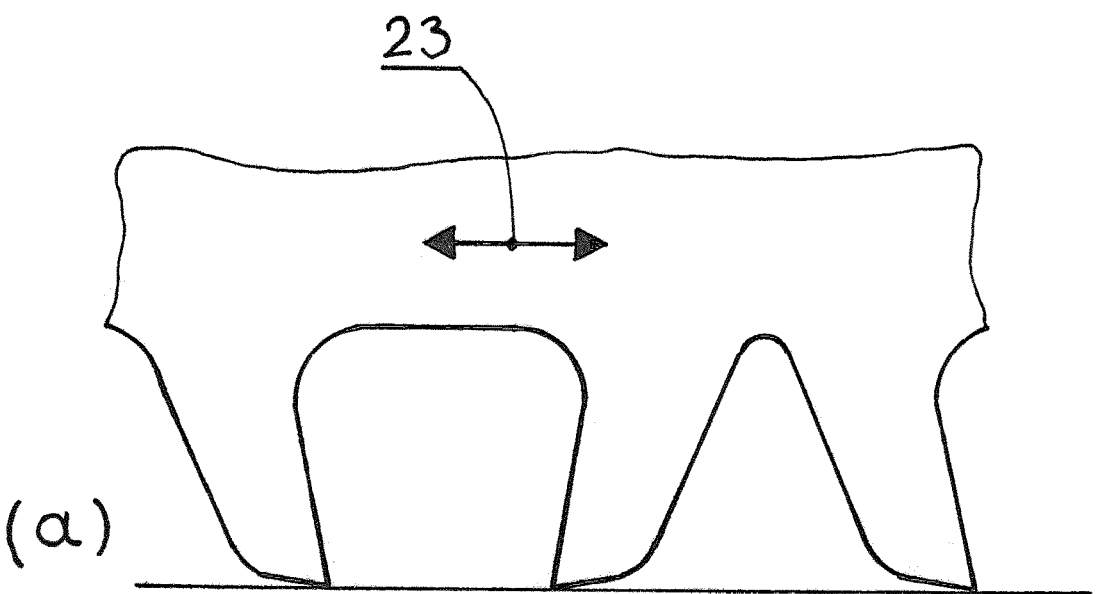
FIG. 7 shows saw teeth with positive rake angles cutting in both directions.
Figure 7:
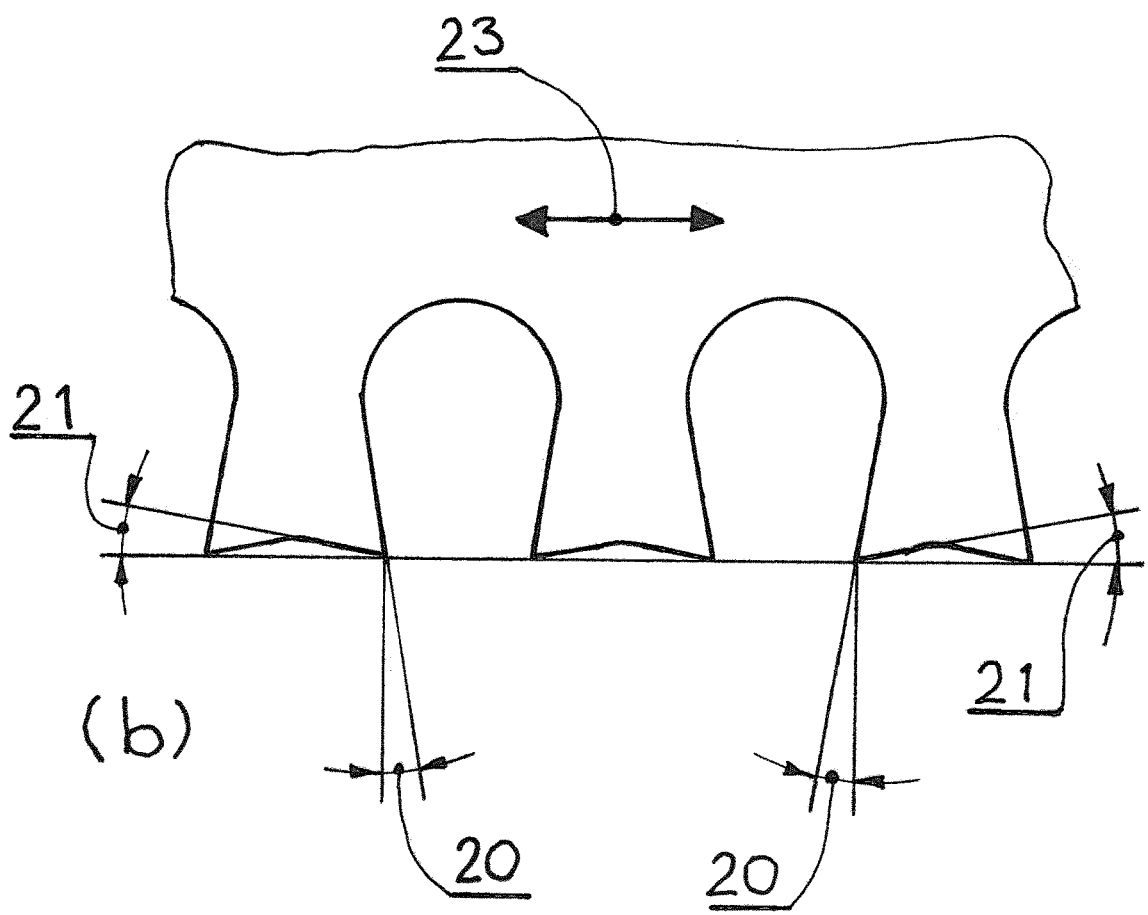

FIG. 7 shows two embodiments where saw teeth are made with positive rake angles but made to cut in both directions indicated by arrows 23. In embodiment (a) it is preferred to make about half of the teeth cut in each direction. In embodiment (b) each tooth is made to cut in both directions with a positive rake angle 20 on both sides of the tooth. The same is true for the relief angles 21.

Having disclosed at least one embodiment of the present invention for a TPLO saw blade and a planar oscillating blade, variations will be understood by one of ordinary skill in the art. Such adaptations, modifications, and improvements are considered part of the invention.

The invention claimed is:

1. An oscillating bone saw blade having a rake angle (12, 20) in the range from 5 to 10 degrees on two or more adjacent saw blade teeth (1, 2), the blade further comprising a positive relief angle (15) on at least some of the saw blade teeth (1, 2), the positive relief angle being in the range from 5 to 15 degrees.

2. The oscillating bone saw blade of claim 1, wherein all of the teeth are oriented to cut in a same direction.

3. The oscillating bone saw blade of claim 1, wherein the teeth are oriented to cut in opposing directions, with a half of the teeth cutting in each direction.

4. The oscillating bone saw blade of claim 1, wherein the teeth are shaped to cut in a first direction and a second direction.

5. The oscillating bone saw blade of claim 1 adapted for medical use.

6. The oscillating bone saw blade of claim 1, which is sterilized and packaged.

7. The oscillating bone saw blade of claim 1, which is a flat or planar saw blade.

8. The oscillating bone saw blade of claim 1, wherein the positive relief angle is 10 degrees.

9. The oscillating bone saw blade of claim 1, wherein a base of each saw blade tooth is cut at an angle configured to direct bone chips sideways out from between adjacent saw blade teeth.

10. The oscillating bone saw blade of claim 1, wherein a cutting face of each saw blade tooth is angled sideways such that the cutting face is configured to direct bone chips sideways out from between adjacent saw blade teeth.

11. The oscillating bone saw blade of claim 10, wherein the cutting faces of adjacent saw blade teeth are angled in opposite directions.

12. An oscillating bone saw comprising the saw blade of claim 1 and a drive unit.

13. A method of performing a bone surgery in human or veterinary medicine, comprising cutting a bone with the oscillating saw blade of claim 1.

14. The method of claim 13, wherein cutting the bone comprises using the oscillating saw blade to make a cylindrical cut for use in a TPLO procedure.

15. The method of claim 13, wherein cutting the bone comprises using the oscillating saw to cut a dome osteotomy for use in a TPLO procedure.

* * * * *